(12) United States Patent
Mamidpelliwar et al.

(10) Patent No.: US 11,225,413 B2
(45) Date of Patent: Jan. 18, 2022

(54) PROCESS FOR PRODUCTION OF HYDRAZINE HYDRATE

(71) Applicants: Council of Scientific & Industrial Research, New Delhi (IN); Gujarat Alkalies and Chemicals Limited, Gujarat (IN)

(72) Inventors: Pradeep Kumar Mamidpelliwar, Telanga (IN); Ravindranath Kajjam, Telanga (IN); Radhakrishna Madabhushi, Telanga (IN); Ashutosh Ugle, Telanga (IN); Shobha Rajendra Pathak, Telanga (IN); Vijaya Garikapati Murthy, Telanga (IN); Thyagarajan Srinivasan, Telanga (IN); Gannoji Veeraiah, Telanga (IN); Shyam Sunder Mamilla, Telanga (IN); Vanka Uma Maheshwara Sarma, Telanga (IN); Parthasaradhy Yellamraju, Telanga (IN); Sunil Sinha, Gujarat (IN); Manish Babulal Shah, Gujarat (IN); Nikhilkumar Navinchandra Shah, Gujarat (IN); Shailesh Ashabhai Patel, Gujarat (IN); Gautam Punjabhai Patel, Gujarat (IN)

(73) Assignees: Council of Scientific & Industrial Research, New Delhi (IN); Gujarat Alkalies and Chemicals Limited, Gujarat (IN)

( * ) Notice: Subject to any disclaimer, the term of this patent is extended or adjusted under 35 U.S.C. 154(b) by 314 days.

(21) Appl. No.: 16/335,225

(22) PCT Filed: Sep. 28, 2017

(86) PCT No.: PCT/IN2017/050431
§ 371 (c)(1),
(2) Date: Mar. 20, 2019

(87) PCT Pub. No.: WO2018/065997
PCT Pub. Date: Apr. 12, 2018

(65) Prior Publication Data
US 2019/0367365 A1    Dec. 5, 2019

(30) Foreign Application Priority Data
Oct. 3, 2016   (IN) .............................. 201611033667

(51) Int. Cl.
| | | |
|---|---|---|
| *C01B 21/16* | (2006.01) | |
| *C07C 249/16* | (2006.01) | |
| *C07C 251/88* | (2006.01) | |

(52) U.S. Cl.
CPC ............ *C01B 21/16* (2013.01); *C07C 249/16* (2013.01); *C07C 251/88* (2013.01)

(58) Field of Classification Search
None
See application file for complete search history.

(56) References Cited

U.S. PATENT DOCUMENTS

| 4,724,133 A | 2/1988 | Schirmann et al. |
| 5,252,309 A | 10/1993 | Krempf et al. |
| 5,986,134 A * | 11/1999 | Kuriyama ............... C01B 21/16 423/407 |

FOREIGN PATENT DOCUMENTS

EP    0 758 642 A2    2/1997

OTHER PUBLICATIONS https://pubchem.ncbi.nlm.nih.gov/compound/Acetamide#section=Physical-Description&fullscreen=true, downloaded on Apr. 7, 2021 (Year: 2021).*

(Continued)

*Primary Examiner* — Amy C Bonaparte
(74) *Attorney, Agent, or Firm* — Knobbe, Martens, Olson & Bear, LLP

(57) ABSTRACT

A process for the production of concentrated aqueous solutions of hydrazine hydrate includes preparation of hydrazine hydrate by a ketazine method using 50-70% hydrogen peroxide, recyclable solid acetamide and ammonium acetate activator for ketazine formation, and catalyst-free hydrolysis of ketazine to provide aqueous solutions of hydrazine hydrate in an energy efficient manner.

11 Claims, 1 Drawing Sheet

(56) References Cited

OTHER PUBLICATIONS

Schirmann, J.-P. et al. 2001 "Hydrazine" in *Ullman's Encyclopedia of industrial Chemistry*, Wiley-VCH Verlag GmbH & Co. KGaA, Weinheim, pp. 79-96.

* cited by examiner

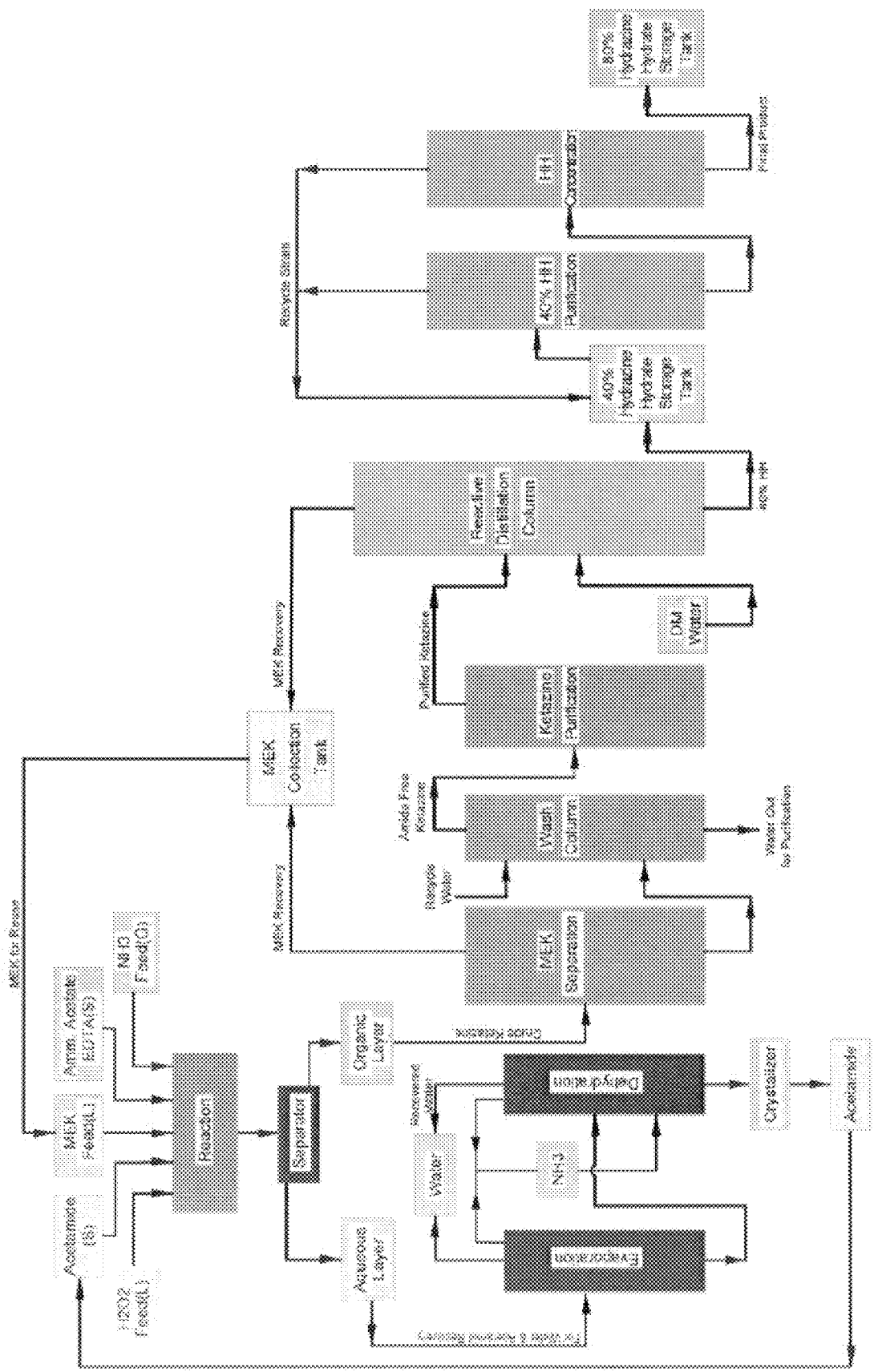

PROCESS FOR PRODUCTION OF HYDRAZINE HYDRATE

FIELD OF THE INVENTION

The present invention relates to an improved method for production of concentrated aqueous solutions of hydrazine hydrate using recyclable solid activator for ketazine formation and catalyst free ketazine hydrolysis.

BACKGROUND OF THE INVENTION

Hydrazine hydrate ($N_2H_4.H_2O$), a colorless liquid having an ammonical odor, is the simplest diamine and unique in its class because of the N—N bond. It was first prepared in 1887 by Curtius from diazo acetic ester. In 1893 Thiele suggested that the oxidation of ammonia with hypochlorite should yield hydrazine hydrate and in 1906 Raschig demonstrated this process, variations of which constitute the chief commercial methods of manufacture in the 1990's. It is a mild base that is miscible in polar solvents such as water, ammonia, amines and alcohols.

During the past fifty years hydrazine hydrate has emerged from an interesting curiosity to a chemical manufactured in tons. Hydrazine hydrate has been known since 1863, and in 1875 Emil Fischer prepared and characterized the aryl compounds of hydrazine hydrate. It was in 1887 Curtius succeeded in isolating hydrazine hydrate itself by the action of alkali on diazo acetic ester.

Raschig, following a suggestion by Thiele, showed that hydrazine hydrate could be produced by the action of sodium hypochlorite on aqueous ammonia, the yield being greater in presence of excess ammonia. Raschig found that 60-70% yields of hydrazine hydrate could be obtained in the presence of glue or gelatin and attributed this effect to the increased viscosity of the solution. Joyner showed that increasing the ammonia:hypochlorite ratio increased the yield of hydrazine hydrate and the yield was proportional to the amount of glue added when this was present in small amounts. The manufacture of hydrazine hydrate by a similar procedure from urea instead of ammonia was patented about this time, yields reported being 70%.

The discovery that hydrazine hydrate containing 15% methanol could be employed as a rocket fuel when mixed with oxidizing agents such as nitric acid, hydrogen peroxide or oxygen, stimulated the expansion of production of hydrazine hydrate in Germany during the Second World War.

The direct fixation of nitrogen and hydrogen to hydrazine is thermodynamically unfavorable. Instead the commercially feasible process involves partial oxidation of ammonia (or urea) using hypochlorite or hydrogen peroxide. Bayer first commercialized such a process, using acetone and hypochlorite as oxidant. Another process developed by Produits Chimiques Ugine Kuhlmann (PCUK) and practiced by Atofina (France) and Mitsubishi Gas (Japan) involves the oxidation of ammonia by hydrogen peroxide in presence of butanone and another component that apparently functions as an oxygen-transfer agent. Oxidation of Benzophenone imine also received much attention, but is not commercially used.

The first large scale use of hydrazine hydrate was as a fuel for powering the rocket, a German ME-163 fighter plane during the World War II. Production in the United States began in 1953 at the Lake Charles, La. plant of the Olin Corporation (now Arch Chemicals) a facility then having a capacity of 2040 metric tons. In 2004, world capacity is approximately 462100 metric tons, reported as $N_2H_4$. Most of this is in the form of hydrazine hydrate. Hydrazine hydrate and its simple methyl and dimethyl derivatives have endothermic heats of formation and high heats of combustion. Hence, these compounds are used as rocket fuels. Other derivatives are used as gas generators and explosives. Hydrazine, a base slightly weaker than ammonia forms a series of useful salts. As a strong reducing agent, Hydrazine hydrate is used for corrosion control in boilers and hot water heating system; also for metal plating, reduction of noble-metals catalysts, and hydrogenation of unsaturated bonds in organic compounds.

Hydrazine hydrate is also an oxidizing agent under suitable conditions. Having two active nucleophilic nitrogen and four replaceable hydrogen, hydrazine is the starting material for many derivatives. Some among them are, as a foaming agent for plastics application, in manufacture of antioxidants, polymers, polymer cross-linkers and chain extenders, as well as in fungicides, herbicides, plant growth regulators and pharmaceuticals. Hydrazine hydrate is also a good ligand; numerous complexes have been studied. Many heterocyclics are based on hydrazine, where the rings contain from one to four nitrogen atoms as well as other heteroatoms. The many advantageous properties of hydrazine hydrate continued its commercial utility. Hydrazine is produced commercially, primarily as an aqueous solution (which is known as hydrazine hydrate) typically in varying % by weight of hydrazine hydrate. The following references serve as the prior-art for the preparation of hydrazine hydrate by various approaches.

U.S. Pat. Nos. 4,189,411; 3,972,878; 3,972,876; 4,093,656; 3,948,902; 6,562,311; 6,482,383; 6,605,265; 5,986,134; EP70155; CN100526237; U.S. Pat. Nos. 4,724,133; 4,725,421; GB1164460; FR1315348; GB1174050; GB1211547; U.S. Pat. No. 3,607,041; FR1506943; and Kirk Othmer, $3^{rd}$ edition, 12, 734-755; Journal of American Chemical Society, 1929, 51, 3394-3409; Ullmann's encyclopedia of industrial chemistry, 1989, A13, 182-183.

Though, several of these methods are practical at laboratory level, only some of them are useful at industrial production. Most of these reported methods are difficult to be practiced at the industrial production due to one or more of the following factors: (a) stringent monitoring of the working solutions; (b) catalyst solutions with varied ranges; (c) low reaction yield due to difficulties in impurity removal; (d) operationally difficult reaction conditions/parameters; (e) catalytic hydrolysis of ketazine to give hydrazine hydrate; (f) high energy requirements.

Objective of the Invention

In view of the limitations in the prior art, the main objective of the present invention is to provide an efficient process for the production of concentrated aqueous solutions of hydrazine hydrate.

Another objective of the present invention is to provide a process for production of hydrazine hydrate, using solid acetamide as the recoverable catalyst for ketazine formation and catalyst free hydrolysis of ketazine to give aqueous solutions of hydrazine hydrate.

Another objective of the present invention is to provide a process which involves catalyst free hydrolysis of ketazine to give hydrazine hydrate with lower volume ratio of water to ketazine (1:1.5), unlike the known methods, where a catalyst and higher water volume ratio is required for hydrolysis.

Yet another objective of the present invention is to provide a method for hydrazine hydrate production, where all unreacted and excess substrates are recoverable and reusable making it a highly energy efficient, clean and eco-friendly process.

SUMMARY OF THE INVENTION

Aiming at the defects and limitations in the prior-art, we have developed a new and highly effective, industrially simple and economically viable process for the production of hydrazine hydrate. Briefly, the present invention features improved process for production of concentrated aqueous solutions of hydrazine hydrates, comprising:
(a) reacting hydrogen peroxide, ammonia, and ketone to form an azine in presence of an activator;
(b) separating the resulting mixture from step (a) into a ketazine layer and a aqueous solution layer;
(c) concentration of ketazine and recovery of methyl ethyl ketone by evaporation;
(d) purification of ketazine by vacuum distillation;
(e) recovery of acetamide from aqueous layer by dehydration;
(f) then returning the recovered methyl ethyl ketone and acetamide to step (a);
(g) hydrolysis of the ketazine to obtain hydrazine hydrate and regenerating the methyl ethyl ketone;
(h) and recycling the methyl ethyl ketone to the stage (a),
(i) concentration of hydrazine hydrate obtained in stage (g) to obtain 40-80% of hydrazine hydrate.
In an embodiment of the present invention, the activator used for ketazine formation stage (a) is acetamide and ammonium acetate.

In another embodiment of the present invention, the acetamide used in stage (a) is a crystalline solid.

In another embodiment of the present invention, the acetamide recovered from dehydration stage (e) is further purified by centrifugation or filtration under vacuum to get crystalline solid.

In an embodiment of the present invention, the hydrogen peroxide is a 50 to 70 weight % $H_2O_2$ solution.

In another embodiment of the present invention, the molar ratio of hydrogen peroxide:methyl ethyl ketone:and ammonia is 1:4:3.

In another embodiment of the present invention, the stage (a) is carried out at temperatures ranging of 0 to 60° C.

In another embodiment of the present invention, the stage (c) evaporation is carried out at temperatures ranging from 85 to 110° C.

In another embodiment of the present invention, the stage (d) vacuum distillation is carried out at temperatures ranging from 75 to 100° C., preferably between 80-90° C.

In another embodiment of the present invention, the volume ratio of ketazine:water in hydrolysis stage (g) is 18:12.

In another embodiment of the present invention, the hydrolysis stage (g) is carried out under a pressure ranging from 2 to 20 bars, preferably between 8 to 12 bars, and temperature ranging from 150 to 200° C., preferably between 175 to 200° C.

In another embodiment of the present invention, the stage (i) purification and concentration is carried out in one cycle.

The present process can be performed easily and is a very economic strategy which is most viable for industrial scale.

BRIEF DESCRIPTION OF THE DRAWING

The drawing is a process flow diagram for hydrazine hydrate (80%).

DETAILED DESCRIPTION OF THE INVENTION

The present process for the production of concentrated aqueous solutions of hydrazine hydrate is described as follows. This process is the most convenient and simple approach based on methyl ethyl ketazine route involving the following stages:

General Process Description

In this process, hydrogen peroxide, gaseous ammonia, and ketone are reacted to form methyl ethyl ketazine which on further hydrolysis forms hydrazine hydrate:

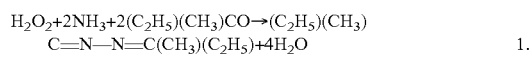

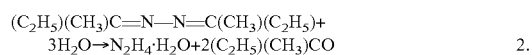

Methyl Ethyl Ketazine Preparation

Hydrogen peroxide in the form of 50 to 70% by weight is used to oxidize ammonia in the presence of a ketone. Methyl ethyl ketone (MEK) or acetone is usually preferred. The reaction of MEK in the presence of hydrogen peroxide and ammonia is carried out at atmospheric pressure and temperatures ranging from 0° C. to 60° C. A molar ratio of Hydrogen peroxide:MEK:Ammonia (gas) of 1:4:3 is taken as feed. Hydrogen peroxide is activated by acetamide and ammonium acetate. The organic phase of the reaction mass, MEK-Methyl Ethyl ketazine is fed to a pressure hydrolysis column at a pressure between 2 and 20 bar (preferably from 8 to 12 bar) and temperatures ranging from 150° C. to 200° C. (preferably from 175° C. to 200° C.). The overall reaction for the methyl ethyl ketazine formation is:

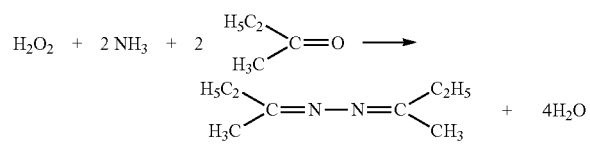

The mechanism of this reaction involves activation of ammonia and hydrogen peroxide because these compounds do not react them self. It appears that acetamide functions as an oxygen transfer agent, possibly as the iminoper acetic acid, which then oxidizes the transient Schiff base formed between MEK and ammonia to give the oxazirdine, with generation of acetamide.

One molecule of ammonia reacts with one molecule of MEK to form Schiff base.

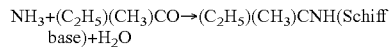

Hydrogen peroxide reacts with acetamide to form iminoper acetic acid.

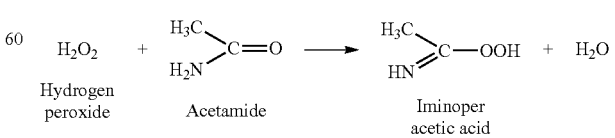

Iminoper acetic acid then oxidizes the Schiff base to give the oxaziridine and regenerates acetamide.

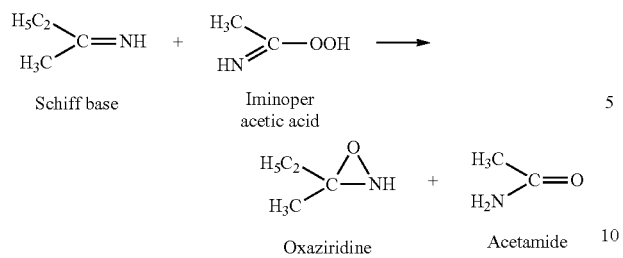

The oxaziridine oxidizes a second molecule of ammonia to form a hydrozone

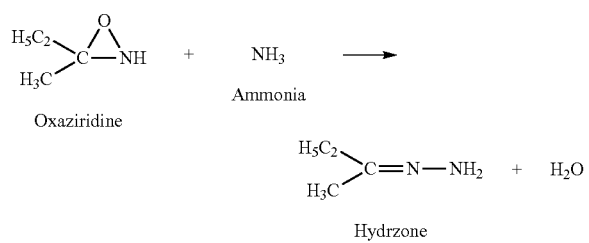

Hydrozone with excess ketone forms the methyl ethyl ketazine.

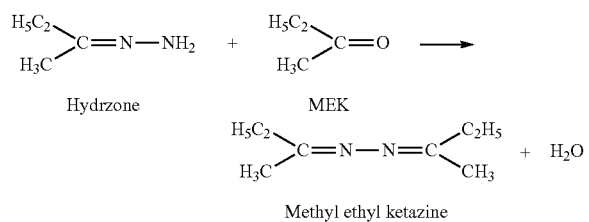

The last two reactions can be clubbed together as follows to give the methyl ethyl ketazine

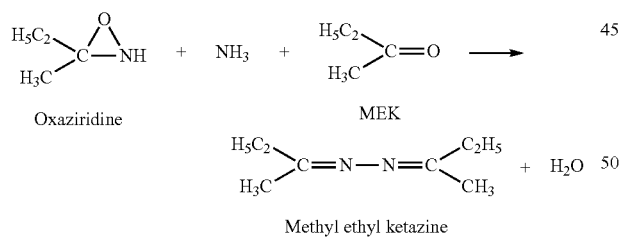

The methyl ethyl ketone (2-butanone) forms an immiscible upper organic layer easily removed by decantation. The lower, aqueous phase containing acetamide and ammonia, is concentrated to remove water formed in the reaction and is then recycled to the reactor after a purge of water soluble impurities. Organic by products are separated from the methyl ethyl ketazine layer by vacuum distillation.

Hydrolysis

The purified methyl ethyl ketazine is hydrolyzed under pressure (8.0-11.0 kg/cm$^2$) to give hydrazine hydrate and methyl ethyl ketone overhead, which is recycled. The hydrazine hydrate is concentrated in final vacuum distillation column.

Process Description:

Preparation of hydrazine hydrate involves the following steps:
1) Methyl ethyl Ketazine preparation.
2) Concentration of methyl ethyl Ketazine/Recovery of MEK.
3) Purification of methyl ethyl ketazine.
4) Recovery and regeneration of acetamide.
5) Hydrazine hydrate preparation.
6) Concentration of hydrazine hydrate from 40 to 80%.

Methyl Ethyl Ketazine Preparation:

A known quantity of Methyl ethyl ketone (MEK) is taken into a reactor and acetamide is charged into the reactor along with appropriate stabilizers. $H_2O_2$ is added in a controlled manner for 5 hrs at a rate of 10-12 kg/hr, simultaneously ammonia is sparged into the reactor at a rate of 6-7 kg/hr. The reaction is exothermic. The reactor is maintained at atmospheric pressure, at a temperature of 50-60° C. throughout the process by circulating chilled water. After addition of both the reactants (i.e., 6 hr), reaction is continued for further 1 hr. the reaction mass is left for settling. After 1 hour, organic and aqueous layers are separated in a separator and stored in separate tanks.

Concentration of Methyl Ethyl Ketazine/Recovery of MEK:

Initially, a known quantity of organic layer is charged into an evaporator. Evaporation of MEK is done under vacuum of 200 to 250 mm Hg at a temperature varying from 60-70° C. Then the material is discharged into a reboiler for purification of methyl ethyl ketazine.

Purification of Methyl Ethyl Ketazine:

Initially, MEK fraction from the mixture is collected under vacuum of 200-250 mmHg and temperature of around 80-90° C. Then gradually vacuum is increased to 20-25 mmHg with temperature in reboiler around 80-90° C. Collect initially intermediate fractions of ketazine and MEK mixture into a tank, and then collect pure enriched methyl ethyl ketazine of 95% and above in a separate tank.

Recovery of Acetamide:

Initially, a known quantity of aqueous layer is charged into a reboiler which is maintained at 100-110° C. to remove 40-45% water. After distilling out water, ammonia is sparged into the reboiler to convert the ammonium acetate which is formed by hydrolysis of acetamide in base conditions during the formation of methyl ethyl ketazine, into acetamide and to recover it; the temperature of the reboiler is increased to 140-145° C. and maintained for 9 hrs. Dehydration is carried out till 65-70% acetamide is present in the bottom product. The product is cooled and crystallized. The solution containing acetamide crystals is either centrifuged or filtered under vacuum. Mother liquor separated from acetamide crystals is recycled back to the dehydration column.

Hydrolysis Section

Hydrazine Hydrate is produced by hydrolysis of Methyl Ethyl Ketazine.

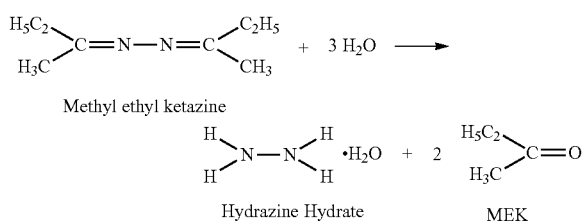

Methyl ethyl ketazine

Hydrazine Hydrate          MEK

General Operational Procedure for Hydrolysis Section

As water is a reactant, the specification of DM water is to be maintained without any deviation in pH (8.2-8.5) and conductivity (preferably >1.0 and always less than 2.0). In a known quantity of DM water addition of 1-2 ml of 80% hydrazine hydrate makes the water alkaline with pH 8.2-8.5.

Perform pressure test of the hydrolysis column and the downstream equipment by taking known quantity of DM water in reboiler and heating by circulation of hot oil, till pressure of 10 bar is attained under total reflux. Note the temperature profile in the column, pot, condenser and reflux drums (pot 180-182° C., column top is steam temperature at 10 barg, reflux 152° C.).

Ketazine is pumped at a rate of 11 lph and DM water is pumped at a rate of 7 lph.

Operational Parameters

The hydrolysis column is operated at a loading capacity of 60% (10.8-11 lph ketazine, 7.2-7.5l ph DMW)

1. Prepare required quantity of 20% HH solution in storage tank and pump to reboiler.
2. Circulate hot oil through the jacket of reboiler. Turn the hot oil heater ON and gradually raise the temperature first to 100° C. and then further. Pot temperature to be maintained at 180° C. and top column temperature between 174-175° C., by setting the hot oil flow rate maintain the required temperature profile in the column.
3. After getting the required temperature profile in the column, start feeding DM water first, followed by ketazine after 5-10 min.
4. Both the feeds are preheated to 100-120° C. by passing steam in jacket of feed lines, and mixing in a static line mixer before entering the column.
5. In the feed section of the column a spray type distributor is fixed to inlet line, which sprays the water-methyl ethyl ketazine mixture on to a bed of ceramic raschig rings packing of 6 mm dia. The column has 2 nos. of 3 m each reaction sections and 2 nos. of 2 m each MEK stripping section above feed section. The column is provided with temperature indicators to measure the temperature profile in the column. The re-boiler is a jacketed vessel where hot oil at known temperature is circulated to heat the contents (20% HH taken at start of the run and 40% HH as the reaction progresses) in the pot.
6. The hydrolysis column is operated under reflux (composition of reflux: water+MEK).
7. The column pressure is maintained between 10.5-11 bar. MEK released at around 160-162° C. is collected at the top and recycled.

Passivation of Reactor with Hydrazine Hydrate:

The hydrolysis column is washed with DM water. A known quantity of 20% Hydrazine Hydrate solution is prepared by diluting fresh 80% Hydrazine Hydrate (Purchased from market) with DM water and charged into the reboiler. The reactor was flushed with $N_2$ for 30 minutes. Hot oil system was started and heating of reboiler was started. After the pressure in the reactor attained 9 Kg/cm² the reactor was kept undisturbed for 12 hrs with constant hot oil circulation for 12 hrs. During this period the reactor was under total reflux condition.

Hydrolysis Experiment:

The DM water is feed at a rate of 6-7 lit/h with preheating it to 120° C. The column was kept under total reflux condition by isolating the reflux drum. After 45 minutes the Ketazine feed was started at the rate of 8.5-10 lit/h with pre heating to 120° C. The pressure in the reactor reaches to 10.5-11 Kg/cm². The column top temperature falls reaches 160-161° C. At this stage take reflux drum in line and start collection of top production. Maintaining the reboiler level, the bottom product is collected continuously.

This process was continued till concentration of Hydrazine Hydrate reaches 40%. The feed rates of ketazine and DM water were maintained at the molar ratio of 1:7.

Purification and Concentration of Hydrazine Hydrate from 40-80%:

The output from the hydrolysis column bottom was used for the concentration experiment.

The unit is run initially with reflux ratio 1:5 for about 20 minutes, when the vapor temperature reaches around 60° C. and the Still temperature in the Reboiler is around 75° C. at 175 mmHg. Then the reflux ratio was changed to 1:1. The vacuum was maintained around 170-175 mmHg. Then start collecting the distillate in the receiver till the vapor temperature reaches around 75° C. Initially a fraction of water is distilled out along with ketazine. This distillation is carried out till there is no ketazine in the bottom product. The distillation is continued to remove the azeotrope of mixture which was collected at a constant vacuum of 170-175 mmHg. After removing the azeotrope the mixture is further treated at a vacuum of 170-175 mm Hg to concentrate it to 80% HH which is obtained as bottom product.

Example: Process Description

Reactor Section

Initially, MEK from tank-farm is fed to storage tank with a vent condenser 3811 kg of MEK is added to a preparation vessel using pump. 1230 kg Acetamide, 29 kg of Ammonium Acetate and 15 kg of EDTA are fed from a conveyor under nitrogen blanket into a hopper and added to the preparation vessel. These solids are kept in suspension and charged into the reactor by gravity in about half an hour. The reactor is maintained at 25° C. under atmospheric pressure. A vent condenser is provided on the reactor with chilled water circulation to avoid loss of MEK during the process.

Then $H_2O_2$ is added to the reactor at 212 kg/hr from storage tank using pump and simultaneously Ammonia gas is sparged into the reactor through a mass flow controller at 110 kg/hr from a header connected to bullets. The reactor jacket is provided with double limpet coil for circulation of hot water in HW limpet and chilled water in CHW limpet. During the first 3 hrs of addition of $H_2O_2$ and $NH_3$, the temperature of the reaction mixture is raised from 25° C. to 50° C. by circulating hot water. Once the temperature reaches 50° C., Hot water is cut off while both $H_2O_2$ & $NH_3$ additions continue. Since the reaction is exothermic, the mixture temperature slowly rises to 58° C. and it is maintained between 55° C.-58° C. by circulating chilled water in CHW limpet while addition of $H_2O_2$ & $NH_3$ is continued. During the reaction process, small amount of $H_2O_2$ decomposes to water & oxygen, and most of the Acetamide converts to Ammonium Acetate. After completion of $H_2O_2$ addition i.e. after approx. 5 hours, ammonia sparging is continued at the same flow rate for 1 more hour. The reactor is run till $H_2O_2$ conc. in the product mixture is not greater than 0.2% which is achieved in almost 30 min after charging of $NH_3$ is discontinued. The $H_2O_2$ conc. is tested by Titration method.

The reaction mixture is then allowed to cool to 25° C. by circulating chilled water. The reaction mass obtained after 7½ hrs (including charging and discharge time) containing unreacted MEK, Ketazine, Ammonia, water, Ammonium Acetate, Acetamide and some unknown compounds, is sent to a separator for layer separation. When the amount of moisture in the organic layer is not greater than 3%, the two layers (Organic and Aqueous) are separated and collected in two different storage tanks. The moisture content is tested using Karl Fischer moisture analysis method. The separation is completed in approx. 60 min. Ketazine yield obtained after completion of reaction is not less than 85% with respect to $H_2O_2$.

The gases formed during reaction process are sent to a scrubber where ammonical liquor is collected and oxygen is let out to atmosphere. The ammonical liquor is collected in a storage tank and sent to ammonical liquor tanker using pump.

Aqueous Processing Section

The Aqueous Layer is taken into Batch Distillation/Dehydration Columns using pump which is operated initially at 120° C. for 3-3.5 hrs to expel ammonia, to evaporate water in the feed and then at 140° C.-150° C. for dehydration of ammonium acetate to recover acetamide. The total batch time is 12 hours.

During this process at about 90-100° C. Ammonium Acetate decomposes to acetic acid and ammonia. To convert acetic acid back to Ammonium acetate, Ammonia gas is sparged into the column from Ammonia buffer tank. The top product containing ammonia, water, traces of MEK and Ketazine is condensed through condenser into. Uncondensed Ammonia in the top product is collected using roots blower and sent to ammonia buffer tank. Condensed top product containing Water with 1% ammonia, traces of MEK and Ketazine is collected in Storage tank. After 3-3.5 h, reboiler temperature is increased to 140° C. At this temperature Ammonium Acetate dehydrates to form Acetamide. Ammonia, water vaporizing are condensed and collected into Storage tank. Uncondensed Ammonia in the top product is collected using roots blower and sent to ammonia buffer tank. The dehydration process is carried out only till concentration of acetamide reaches 70% is obtained in the bottom product. The Bottom product is a homogenous mixture of Acetic Acid, Acetamide, Ammonium Acetate and water.

This mixture is sent to crystallizer where it is first cooled to 60° C. by circulating cooling water in the jacket for one hour and then to 15° C. using brine and maintained at this temperature for 5 h. This crystallized product is sent to a centrifuge where wet solids i.e., acetamide are separated and collected in bags for recycle.

The mother liquor obtained from the centrifuge containing water with Acetic Acid, Ammonium Acetate, some Acetamide, is collected in storage tank and sent to Batch Dehydration column using pump which is dedicated to mother liquor dehydration to recover acetamide. The column is maintained at 140-150° C. and the batch time is 9 hrs. The top product containing water with 1% ammonia and acetic acid is condensed. Acetic acid is refluxed back to the column and ammonical liquor is collected in storage tank. Bottom product containing Acetic Acid, Acetamide, Ammonium Acetate and water is sent to crystallizer where it is first cooled to 60° C. by circulating cooling water in the jacket for one hour and then to 15° C. using brine and maintained at this temperature for 5 hours. This crystallized product is sent to centrifuge where wet solids are separated and collected in bags for recycle. Mother liquor separated is collected in storage tank and sent for recycle.

Organic Layer Processing Section

Organic layer from containing MEK, ketazine Mixture is taken into a continuous distillation column operated at 200-250 mmHg and 60-70° C. to remove MEK-water azeotrope, and $NH_3$. The condensed top product is collected in a storage tank. The distillation column is operated such that moisture content in the bottom product is not greater than 2%. This is measured using Karl Fischer moisture analysis method. This MEK is checked for conformance to the MEK specifications for reuse and collected in a storage tank. The bottom product containing ketazine, acetamide, some amount of MEK, unknown compounds is collected in a storage tank.

This mixture is then sent to a continuous counter current packed column where it is water washed. Water is added to the column from top and the feed mixture is fed from bottom. The Acetamide present in the feed is collected into the aqueous layer along with traces of ketazine and MEK and collected as bottom product into a storage tank. The top product i.e. the organic layer which is free from Acetamide is collected into a storage tank.

This mixture containing ketazine, some amount of MEK, water, unknown compounds is now fed into a distillation column which is operated at 80-85° C. and 20-25 mmHg to purify the ketazine. The condensed top product from condenser containing ketazine, some amount of MEK, water and some unknown compounds is collected in a storage tank for Hydrolysis. The bottom product containing unknown compounds, some ketazine is collected in a storage tank and sent to an Evaporator to recover ketazine as top product. The evaporator is operated at 80-85° C. and 20-25 mmHg. The Ketazine thus recovered from top through condenser is sent for hydrolysis. The bottom heavies (Unknown compounds) from the evaporator are sent for incineration.

Hydrolysis Section

Initially, Ketazine and DM water is then sent to static mixer where HH is also added. The output pH of water coming from static mixer going to distillation column is maintained at 8.2-8.5 by adjusting the quantity of HH added to water. The two streams, ketazine, DM water are preheated passed through static mixer into reactive distillation column.

Preparing the Reactive Distillation Column for First Run:

First, fill 50% of the column reboiler with 20% HH. Then, purge the column with nitrogen for 20 minutes. Discontinue nitrogen purging, and heat the column slowly using hot oil system. Once the column bottom temperature reaches 100° C., vent out the steam generated in the column which will also expel any trapped nitrogen. Close the vent valves and continue heating. When the column bottom temperature reaches 180° C., column pressure will be around 8.0 to 9.0 bar pressure. DM water preheated to 70-80° C., is fed into the column through a static mixer. After the column stabilizes at around 180° C. & 10.0 bar pressure, start feeding Ketazine preheated to 70-80° C., in pre-heater into the column through the static mixer. Maintain 180-190° C. at the bottom and 160-165° C. at the top of the column at a pressure of 10.5 to 11 bar thorough out the process.

The top product containing MEK, un-reacted water and soluble ketazine is condensed in condensers are collected in a reflux drum. Ketazine and Water are refluxed back into the column and MEK is separated. Bottom product containing 40% H.H along with some methyl ethyl ketazine is collected in storage tank. This Crude 40% HH is sent to concentration to 80% HH.

Purification and Concentration Section

Initially, a mixture of 40% HH, methyl ethyl ketazine, water, hydrazone and some unknown compounds is fed into the reboiler of Batch Distillation Column from storage tank. The column is run for 7 hrs under a vacuum of 180 mmHg, at a temperature of 65-70° C. The distillation is carried out till no methyl ethyl ketazine is present in bottom product and it is measured using GC method. The top product containing water, methyl ethyl ketazine is condensed and stored in storage tank. This mixture is sent back for reactive distillation.

The bottom product containing around 60-70% HH and water is collected in storage tank and sent to a Continuous azeotropic Distillation Column where heavies are separated. The column is maintained under a vacuum of 180 mmHg, at a temperature of 65-70° C. The Column is operated such that 90% of the feed is collected as top product. The top product containing 70% HH and balance water is condensed and collected in storage tank. The bottom product containing HH, water and solids is stored in a storage tank and sent to pressure leaf where the solids are separated. The mother liquor is collected in storage tank and sent for recycle.

The top product is sent to a Continuous Distillation Column where 70% HH is concentrated to 80% HH. The column is maintained under a vacuum of 180 mmHg, at a temperature of 65-70° C. The percentage of HH in the bottom is 80% and is measured using GC method. The bottom product containing 80% HH, some water is collected in storage tank. The top product containing about 30% HH and water is condensed in condenser and collected in storage tank. This mixture is sent for recycle.

Analytical Methods

To determine the rate of formation of ketazine, it is necessary to estimate its amount present in the reaction mixture. So a suitable analytic technique is the main requirement for the accurate determination of the product. Methyl ethyl ketazine in the reaction mixture have been estimated by using gas chromatography which gave results of good accuracy. The organic layer was analyzed for the amount of methyl ethyl ketazine and the aqueous layer was analyzed for the peroxide present.

Raw Material Analysis

MEK Analysis

A Gas Chromatography method was used to analyze MEK. The GC conditions used as follows:
Column: TENAX TA, 2 m× ⅛" SS column
Oven Temp: Initial 70° C. hold for 3 min then rise to 250° C. @15° C./min
Injection port Temp: 230° C.
Carrier gas Flow: 15 ml/min ($H_2$)
Sample size: 0.2 μL
Quantification: External area normalization technique Acetamide Analysis The pure substance of Acetamide is dissolved in methanol and analyzed by GC method. The area for the pure acetamide is calculated and used to quantify the acetamide content in feed sample. The 70% solution of acetamide dissolved in water as feed is analyzed by injecting into GC without methanol. The quantification of acetamide content is calculated using the formula.

% Acetamide=$(A_{sample}/A_{pure})\times100$ $A_{sample}$=Area count for acetamide in sample from GC
$A_{pure}$=Area count for acetamide in Pure from GC The GC conditions are same as mentioned above.

Intermediate Analysis

Nature of the process requires two layers of samples always to be analyzed. One is organic layer and the other one is aqueous layer. In addition to that, analysis of the samples collected during the process of concentrating organic layer and removal of acetamide from aqueous layer and at various stages of process as and when required, is also to be done. All these samples were analyzed by GC method using the following conditions.
Column: TENAX TA, 2 m× ⅛" SS column
Oven Temp: Initial 70° C. hold for 3 min then rose to 250° C. @ 15° C./min.
Injection port Temp.: 230° C.
Carrier gas Flow 15 ml/min ($H_2$)
Sample size: 0.2 μl
Quantification: External area normalization technique Analysis of Hydrogen Peroxide Hydrogen peroxide in the reaction mixture was estimated by titrating against standard $KMnO_4$ solution. 0.1 N $KMnO_4$ solution is used for this purpose. The procedure for carrying out titrations has been taken from worksheets of Solvay Specialty Chemicals Limit.

Reagents Used

In the Peroxide Analysis, following chemicals are used
1. Standard $KMnO_4$ solution (0.1 N)
2. Conc. $H_2SO_4$ (A.R. Grade)
3. Sodium Oxalate ($Na_2C_2O_4$) (A.R. Grade)
4. Distilled Water Reaction Involved The reaction between hydrogen peroxide and potassium permanganate can be represented a follows

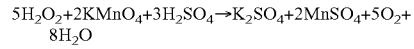

The net ionic equation is

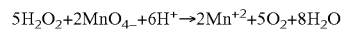

Preparation of 0.1 N $KMnO_4$ Solutions
Molecular Weight of $KMnO_4$=158.04 g
Equivalent Weight of $KMnO_4$=Molecular Weight of $KMnO_4$/Valency
=158.04/5=31.608 g For making 1 N $KMnO_4$ solution, we have to dissolve 31.608 grams of $KMnO_4$ in 1 L of Distilled water. Thus for making 0.1 N $KMnO_4$ solution, we have to dissolve 3.1608 g of $KMnO_4$ in 1 liter i.e. 1000 ml of distilled water. This $KMnO_4$ solution formed is thus stored in amber colored bottles to protect from photo degradation.

Principle 2 moles of $KMnO_4$ reacts with 5 moles of $H_2O_2$.
Molecular Weight of H2O2=34.002 g
Molecular Weight of $KMnO_4$=158.04 g
Thus 2×158.04 g of $KMnO_4$ reacts with 5×34.002 g of $H_2O_2$ Now; 1 L of 0.1 N $KMnO_4$ solutions contains 3.1608 g of $KMnO_4$. And thus 1 ml of 0.1N $KMnO_4$ solution contains 3.1608/1 000 g of $KMnO_4$. Thus 1 ml of 0.1 N $KMnO_4$ is required to titrate.

=$[\{(5\times34.002)/(2\times158.04)\}\times(3.1608/1000)]$ g of $H_2O_2$.

=or 1 ml of 0.1 N $KMnO_4\times1.7001\times10^{-3}$ g of $H_2O_2$.

Standardization of $KMnO_4$ Solution

Potassium permanganate is standardized by its reaction with sodium oxalate, $Na_2C_2O_4$. For this purpose, take about 0.3 g of dry sodium oxalate in 500 ml iodine flask. This sodium oxalate had been dried in oven at 105° C. for 4 h and after cooling is kept in a desiccator with calcium chloride to avoid any moisture absorption. To this sodium oxalate add 20 ml of distilled water and 5 ml of cone. $H_2SO_4$. Now start adding $KMnO_4$ solution, prepared as per the procedure given, from a 50 ml burette until the first appearance of faint pink color that persists for 30 seconds. Note the volume of $KMnO_4$ consumed ($V_1$) for the titration. In this titration, temperature of the solution rises on the addition of cone. $H_2SO_4$. The temperature of the solution in the flask should not fall below 70° C. before the end point is reached. The reaction involved is as follows:

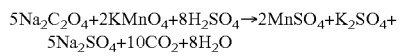

$$5Na_2C_2O_4 + 2KMnO_4 + 8H_2SO_4 \rightarrow 2MnSO_4 + K_2SO_4 + 5Na_2SO_4 + 10CO_2 + 8H_2O$$

The net ionic equation is

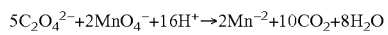

$$5C_2O_4^{2-} + 2MnO_4^- + 16H^+ \rightarrow 2Mn^{-2} + 10CO_2 + 8H_2O$$

Hydrogen Peroxide Analysis Calculations

To find out the amount of peroxide present in the given sample take about 0.2-0.3 ($W_2$) g of $H_2O_2$ in a 250 ml iodine flask. To this add 20 ml of distilled water and then add 5 ml of Concentrated $H_2SO_4$ (A.R. Grade) carefully. Titrate the solution against standard $KMnO_4$ solution till a light pink color persists for 30 seconds. Note the volume of $KMnO_4$ consumed ($V_2$) for the titration.

1 ml of 0.1 N $KMnO_4 \times 1.7001 \times 10^{-3}$
1 ml of 1 N $KMnO_4 \times 1.7001 \times 10^{-2}$ When, $V_2$=Volume of $KMnO_4$ used (ml)
N=Normality of $KMnO_4$ solution.
$W_2$=Weight of sample taken for analysis (g).

$$H_2O_2 = \frac{V_2 \times N \times 1.7011 \times 10^{-2} \times 100}{W_2}$$

Product Analysis

The final product obtained is Hydrazine Hydrate which is also analyzed using GC with following conditions:
Column TENAX TA, 2 m× ⅛" SS column
Oven Temp Initial 70° C., hold for 3 min, then raise to 250° C. @ 15° C./min
Injection port Temp: 230° C.
Carrier gas Flow 15 ml/min ($H_2$)
Sample size 0.2 μl
Quantification: External area normalization technique Significance of the Work Carried Out In view of the importance and lack of efficient scalable production methods for the preparation of hydrazine hydrate, the present process developed by us serves as a highly energy efficient, clean, eco-friendly and scalable method for the production of concentrated aqueous solutions of hydrazine hydrate. This method also serves as a catalyst free approach for the hydrolysis of ketazine to produce hydrazine hydrate.

Advantages of the Invention

The various advantages of the present invention are given below:

1. The main advantage of the present invention is that it provides an energy efficient, clean, eco-friendly and scalable process for the production of concentrated aqueous solutions of hydrazine hydrate.
2. The advantage of the present invention is that the process employs recyclable solid crystalline acetamide as the catalyst, unlike the known methods wherein, the catalyst solutions are used.
3. Another advantage of the present invention is the employment of simple reaction and operational parameters.
4. Purification and/or recovery of the products and/or by products form at all the stages of the process are straight forward.
5. This process involves catalyst free hydrolysis of ketazine to give hydrazine hydrate with lower volume ratio of water to ketazine (1:1.5), unlike the known methods, where a catalyst and higher water ratio is required for hydrolysis.
6. This is an attractive and economic method for the production of concentrated aqueous solutions of hydrazine hydrate.

The invention claimed is:

1. A process for preparation of concentrated aqueous solutions of a hydrazine hydrate, the process consisting of:
    (a) reacting a hydrogen peroxide solution, ammonia, and methyl ethyl ketone in the presence of an activator to form a mixture, wherein the activator comprises acetamide and ammonium acetate, and wherein the hydrogen peroxide solution, methyl ethyl ketone, and ammonia are present in a molar ratio of 1:4:3;
    (b) separating the mixture from step (a) into a ketazine layer and an aqueous solution layer;
    (c) concentrating the ketazine layer to obtain ketazine and recovering the methyl ethyl ketone by evaporation;
    (d) purifying the ketazine by vacuum distillation to obtain a purity of more than 95%;
    (e) recovering the acetamide from the aqueous solution layer by dehydration;
    (f) recycling the recovered methyl ethyl ketone and the recovered acetamide to step (a);
    (g) hydrolyzing the ketazine with water in a volume ratio of 1.5:1 to obtain the hydrazine hydrate and regenerating the methyl ethyl ketone;
    (h) recycling the methyl ethyl ketone to the step (a), and
    (i) purifying and concentrating the hydrazine hydrate obtained in step (g) to obtain 80% concentrated hydrazine hydrate in one cycle, and wherein the hydrolysis is catalyst free.

2. The process according to claim 1, wherein the acetamide used in step (a) is a crystalline solid.

3. A process for preparation of concentrated aqueous solutions of a hydrazine hydrate, the process consisting of:
    (a) reacting a hydrogen peroxide solution, ammonia, and methyl ethyl ketone in the presence of an activator to form a mixture, wherein the activator comprises acetamide and ammonium acetate, and wherein the hydrogen peroxide solution, methyl ethyl ketone, and ammonia are present in a molar ratio of 1:4:3;
    (b) separating the mixture from step (a) into a ketazine layer and an aqueous solution layer;
    (c) concentrating the ketazine layer to obtain ketazine and recovering the methyl ethyl ketone by evaporation;
    (d) purifying the ketazine by vacuum distillation to obtain a purity of more than 95%;
    (e) recovering the acetamide from the aqueous solution layer by dehydration;
    (f) recycling the recovered methyl ethyl ketone and the recovered acetamide to step (a);

(g) hydrolyzing the ketazine with water in a volume ratio of 1.5:1 to obtain the hydrazine hydrate and regenerating the methyl ethyl ketone;

(h) recycling the methyl ethyl ketone to the step (a), and (i) purifying and concentrating the hydrazine hydrate obtained in step (g) to obtain 80% concentrated hydrazine hydrate in one cycle, and wherein the hydrolysis is catalyst free;

wherein the acetamide recovered from dehydration step (e) is further purified by centrifugation or filtration under vacuum to get crystalline solid before being recycled in step (f).

4. The process according to claim 1, wherein the hydrogen peroxide solution is a 50 to 70 weight % $H_2O_2$ solution.

5. The process according to claim 4, wherein step (a) is carried out at temperatures ranging from 0 to 60° C.

6. The process according to claim 4, wherein step (c) evaporation is carried out at temperatures ranging from 85 to 110° C.

7. The process according to claim 4, wherein step (d) vacuum distillation is carried out at temperatures ranging from 75 to 100° C.

8. The process according to claim 4, wherein the hydrolysis step (g) is carried out under a pressure ranging from 2 to 20 bars, and at a temperature ranging from 150 to 200° C.

9. The process according to claim 4, wherein step (d) vacuum distillation is carried out at temperatures ranging from 80-90° C.

10. The process according to claim 4, wherein the hydrolysis step (g) is carried out under a pressure ranging from 8 to 12 bars.

11. The process according to claim 4, wherein the hydrolysis step (g) is carried out at a temperature ranging from 175 to 200° C.

* * * * *